United States Patent [19]

Chang et al.

[11] Patent Number: 5,484,727
[45] Date of Patent: Jan. 16, 1996

[54] CLONED GENE ENCODING ACYLCOENZYME A: CHOLESTEROL ACYLTRANSFERASE (ACAT)

[75] Inventors: Ta-Yuan Chang; Catherine C. Y. Chang, both of Hanover, N.H.

[73] Assignee: Trustees of Dartmouth College, Hanover, N.H.

[21] Appl. No.: 121,057

[22] Filed: Sep. 10, 1993

Related U.S. Application Data

[63] Continuation-in-part of Ser. No. 959,950, Oct. 14, 1992, abandoned.

[51] Int. Cl.$^6$ .............................. C12N 9/10; C12N 15/54; C12N 15/85; C12Q 1/48
[52] U.S. Cl. ..................... 435/252.3; 435/15; 435/193; 435/69.1; 435/320.1; 536/23.2; 935/14; 935/32; 935/70; 935/59
[58] Field of Search .................................... 435/69.1, 193, 435/252.3, 320.1, 15; 536/23.2, 24.32, 24.33

[56] References Cited

U.S. PATENT DOCUMENTS

| | | | |
|---|---|---|---|
| 4,652,639 | 3/1987 | Stabinsky | 536/23.1 |
| 5,023,243 | 6/1991 | Tullis | 514/44 |
| 5,075,227 | 12/1991 | Hagen | 435/172.3 |
| 5,173,408 | 12/1992 | Lange, III et al. | 435/198 |
| 5,215,915 | 7/1993 | Tiberi et al. | 435/252.3 |
| 5,217,865 | 6/1993 | Myerowitz | 435/6 |
| 5,281,520 | 1/1994 | O'Hara et al. | 435/69.1 |

FOREIGN PATENT DOCUMENTS

| | | |
|---|---|---|
| WO91/07483 | 5/1991 | WIPO. |
| WO93/07280 | 4/1993 | WIPO. |
| WO93/06123 | 4/1993 | WIPO. |

OTHER PUBLICATIONS

Fortkamp, E., et al., 1986, DNA, 5(6): 511–517.
Spector, A. A., et al., 1979, Progress in Lipids Research, 18(1):31–53.
Chang, T.-Y., and Doolittle, G. M., 1983, The Enzymes, 16:523–539.
Cadigan, K. M., et al., 1988, The Journal of Biological Chemistry 263(1):274–282.
Cadigan, K. M., et al., 1990, The Journal of Cell Biology, 110(2):295–308.
Cadigan, K. M., et al.. 1988, Journal of Lipid Research, 29(12):1683–1692.
Chautan, M., et al., 1988, Analytical Biochemistry, 173(2):436–439.
Little, M.–T. E., et al., 1992 American Journal of Physiology 262(4):G599–G602.
Cadigan, K. M., et al., 1989 The Journal of Cell Biology, 108(6):2201–2210.
Metherall, J. E., et al., 1991, The Journal of Biological Chemistry, 266(10):12734–12740.
O'Brien, P. M., and Sliskovic, D. R., 1992, in *Current Opinion in Therapeutic Patents*, pp. 507–526, Current Drugs, Ltd., publishers.
Babbitt, P. C., et al., 1992, Biochemistry, 31(24):5594–5604.

(List continued on next page.)

*Primary Examiner*—Rpbert A. Wax
*Assistant Examiner*—William W. Moore
*Attorney, Agent, or Firm*—Lahive & Cockfield; Giulio A. DeConti, Jr.; Ann Lamport Hammitte

[57] ABSTRACT

This invention pertains to purified, biologically active acyl coenzyme A: cholesterol acyltransferase (ACAT) and to nucleic acid (DNA or RNA) encoding acyl coenzyme A: cholesterol acyltransferase. The nucleic acid, or a fragment thereof, may be ligated with an expression vector and transfected into cells to express acyl coenzyme A: cholesterol acyltransferase activity in intact cells and in cell-free extracts.

2 Claims, 11 Drawing Sheets

OTHER PUBLICATIONS

Doolittle, G. M., 1981, Dissertation Abstracts International, 24(4): 1429–B.

Schild, D., et al., 1990, Proceedings, National Academy ofSciences, U.S.A., 87(8):2916–2920.

International Search Report issued during prosecution of PCT/US 93/09704.

Catherine Chang and T. Y. Chang, (1993), "Molecular Cloning and Functional Expression of Human Acyl–Coenzyme A:Cholesterol Acyltransferase (ACAT) cDNA", *The FASEB Journal*, vol. 7, No. 7, p. A1147, Abstract No. 551.

Chang C. C., et al., (1993), "Molecular Cloning and Functional Expression of Human Acyl–Coenzyme A:Cholesterol Acyltransferase cDNA in Mutant Chinese Hamster Ovary Cells", *The Journal of Biological Chemistry*, vol. 268, No. 28, pp. 20747–20755.

Kinnunen, P. M., et al., (1988), "Chemical Modification of Acyl–CoA:Cholesterol–O–Acyltransferase. 1.) Identification of Acyl–CoA:Cholesterol O–Acyltransferase Subtypes by Differential Diethyl Pyrocarbonate Sensitivity", *Biochemistry*, vol. 27, pp. 7344–7350.

Jolly, D. J., et al., (1982), "Isolation of a genomic clone partially encoding human hypoxanthine phosphoribosyltransferase", *Proceedings of the National Academy of Sciences*, vol. 79, pp. 5038–5041.

FIG. 3

```
gaaaccctgcaaaggagtccctagagacacctagtaatggtcgaattgacataaaacagt
tgatagcaaagaagataaagttgacagcagaggcagaggaattgaagccatttttatga
aggaagttggcagtcactttgatgattttgtgaccaatctcattgaaaagtcagcatcat
tagataatggtgggtgcgctctcacaaccttttctgttcttgaaggagagaaaaacaacc
atagagcgaaggatttgagagcacctccagaacaaggaaagatttttattgcaaggcgct
ctctcttagatgaactgcttgaagtggaccacatcagaacaatatatcacatgtttattg
ccctcctcattctctttatcctcagcacacttgtagtagattacattgatgaaggaaggct
ggtgcttgcaagttacgcctcctgtcttatgcatttggcaaatttcctaccgttgtttg
gacctggtggatcatgttcctgtctacatttcagttccctattttctgtttcaacattg
gcgcactggctatagcaagagttctcatccgctgatccgttctctcttccatggctttct
tttcatgatcttccagattggagttctaggttttggaccaacatatgttgtgttagcata
tcctgccaccagcttcccggttcatcattattcgagcagatcgttttgtaatgaaggccc
actcatttgtcagagagaacgtgcctcgggtactaattcagctaaggagaaatcaagcac
tgttccaatacctacagtcaaccagtatttgtacttcttatttgctcctacccttatcta
ccgtgacagctatcccaggaatcccactgtaagatggggttatgttgctatgaagtttgc
acaggtctttggttgcttttctatgtgtactacatctttgaaaggctttgtgccccctt
gtttcggaatatcaaacaggagcccttcagcgctc
```

FIG. 6A

```
gggtagagacggggtttcaccgtgttagccaggatggtctggatctcctgacctcgtgatccac
ccacctcggcctcctaaagtgctgggattacagacatgagccaccgcgcccagccctattcatc
ccttttcaaaagtcagaccctaggaagctggagggaggtggggcatggttttacagtgaatttc
tgatttcactcagggtgataaatcagactcttggggaagcgggtggtggctctggacagcagca
ggaatggggatccagttagcaacaaatccatggacctatgacaggctgaaagccacccttctc
catctttgggaggttgccaatgtctgatttaacactatccaatgaatgatcattgaaagtaaaa
aataactatcaactagcagaaaatataaatggtaagcattagcacatatttcacatgtttatat
ttggctctcagattgacctataaaacaaagtctgggaaattctatatgatcctgaaaaaatgat
acgctggtctggatggtagaataagttggagaaatgtttaagccaaaatgcagtcttaccaatg
acttttatttatttattaattttcaggattttttggtatacaggtggttttttggttacatgg
aaaagttctttactggtgatttctgagattttagttcacccttatcctgagcagtgtacactg
ttcccaatatgtagccttttatccctcacccctctaagttcaagaagactatggtcctgcaga
aagctttatatgtaattaacatatctttatctttatctttataggcagtagactcatcttttga
aacagattccattaagagtgaatgtgtaccctccctctagcctttattattactgttttgcta
ttacatgtgttagtgtatgtgaatttaatgcttaaaaatgtatcccattggctactatggcaaa
aggttgactcataagagtttagcacgggttaagatctgaaagttttctNNcccagcctcttatc
actggcNagacttcacaattcatggaagccaccagtgagatgacattagcacgggtagtcgatt
tgcagcctcttatcactgNNNNagacttcacaattcatggaacaggaatgacatttcgctcagg
cagttactgtttttatattctataactcgaggagctcagggctttcggaaatcattaaactttc
cttgtccttttaaagttggagccagcaattgtagacagccttccagtgggttatcttttgtgt
ctccttacctgtggagaagcctattagctggatatattattaaatagctatatttatatatatc
cagggcacccgaattcgggagagcttcccggagtcgaccttcctgctggctgctctgtgacgct
tcccgctctgcctcttggccgaagtcgcgctgccgggcgcgggcctcagacaatacaatggtg
ggtgaagagaagatgtctctaagaaaccggctgtcaaagtccagggaaaatcctgaggaagatg
aagaccaggagaaaccctgcaaaggagtccctagagacacctagtaatggtcgaattgacataa
aacagttgatagcaaagaagataaagttgacagcagaggcagaggaattgaagccattttttat
gaaggaagttggcagtcactttgatgattttgtgaccaatctcattgaaaagtcagcatcatta
gataatggtgggtgcgctctcacaacctttttctgttcttgaaggagagaaaaacaaccatagag
cgaaggatttgagagcacctccagaacaaggaaagatttttattgcaaggcgctctctcttaga
tgaactgcttgaagtggaccacatcagaacaatatatcacatgtttattgccctcctcattctc
tttatcctcagcacacttgtagtagattacattgatgaaggaaggctggtgcttgcaagttacg
cctcctgtcttatgcatttggcaaatttcctaccgttgtttggacctggtggatcatgttcct
gtctacattttcagttccctatttctgtttcaacattggcgcactggctatagcaagagttct
catccgctgatccgttctctcttccatggctttctttcatgatcttccagattggagttctag
gttttggaccaacatatgttgtgttagcatatcctgccaccagcttccggttcatcattattc
gagcagatcgtttgtaatgaaggcccactcatttgtcagagagaacgtgcctcgggtactaat
tcagctaaggagaaatcaagcactgttccaatacctacagtcaaccagtatttgtacttcttat
ttgctcctacccttatctaccgtgacagctatcccaggaatcccactgtaagatgggttatgt
tgctatgaagtttgcacaggtctttggttgcttttctatgtgtactacatctttgaaaggctt
tgtgccccttgtttcggaatatcaaacaggagcccttcagcgctcgtgttctggtcctatgtg
```

FIG. 6B

```
tatttaactccatcttgccaggtgtgctgattctcttccttacttttttgccttttgcactg
ctggctcaatgcctttgctgagatgttacgctttggtgacaggatgttctataaggattggtgg
aactccacgtcatactccaactattatagaacctggaatgtggtggtccatgactggctatatt
actatgcttacaaggactttctctggttttctccaagagattcaaatctgctgccatgttagc
tgtctttgctgtatctgctgtagtacacgaatatgccttggctgtttgcttgacttttctat
cccgtgctgttcgtgctcttcatgttctttggaatggctttcaacttcattgtcaatgatagtc
ggaaaaagccgatttggaatgttctgatgtggacttctcttttcttgggcaatggagtcttact
ctgctttattctcaagaatggtatgcacgtcggcactgtacctctgaaaaatcccacatttt
ggattatgtcctgtcacgttcctggacttgtcgttacgtgttttagaagcttggactttgtttc
ctccttgtcactgaagattgggtagctcctgatttggagccagctgtttccagttgttactga
agttatctgtgttatttggaccactccaggctttacagatgactcactccattcctaggtcact
tgaagccaaactgttggaagttcactggagtcttgtacacttaagcagaggagaacttttttg
tggggctgggtgggggagaagaccgactaacagctgaagtaatgacagattgttgctgggtca
tatcagctttatcccttggtaattatatctgttttgtttcttgactctgtccaatcagagaata
aacatcatagtttcttggccactgaattagccaaaacacttaggaagaaatcacttaaatacct
ctggcttagaaattttttcatgcacactgttggaatgtatgctaattgaacatgcaattgggga
agaaaaattagaatgatttttgctatttctagtagaaagaaaatgtctgttttccaaagataa
tgttatacatcctatttgtaatttttttgaaaaaagttcaatgttcagttttccttagttttt
accttgttctctataggtcagtatttctgtgaagcaaaagatgcctttaccatgaattct
tgagtttacatcaataatattgtatattaaggggatcagaagtaggaaggaaaaataagagat
agcagaggaaaagaaaaacatttcctcttataacttctgaagtaatttgtaaaaagatttgt
agagtcaatcatgtgtttaaattattttatcacaaacttaacatggaagatattccttttaac
tttgtggtaacttctttgaagttatttagaaatatcctttggaacaattattttattgtctaat
aaatattgacttctcttgaattattttgcagactagtgagtctgtac
```

CLONED GENE ENCODING ACYLCOENZYME A: CHOLESTEROL ACYLTRANSFERASE (ACAT)

Government Support

The work leading to this invention was supported, in part, by research grants from The United States government.

REFERENCE TO RELATED APPLICATIONS

This application is a continuation-in-part of Ser. No. 07/959,950 filed Oct. 14, 1992, now abandoned, and entitled "Acyl Coenzyme A: cholesterol Acyltransferase (ACAT)".

BACKGROUND OF THE INVENTION

Acyl coenzyme A: cholesterol acyltransferase (ACAT) is an intracellular enzyme that uses cholesterol and fatty acyl-coenzyme A (CoA) to form cholesterol esters. Accumulation of cholesterol esters as cytoplasmic lipid droplets within cells of human aortic tissue is a characteristic feature of early lesions of atherosclerotic plaque. In intestines of vertebrate animals, the extent of absorption of dietary cholesterol can be shown to be significantly reduced by inhibiting intestinal ACAT activity. In livers of vertebrate animals, formation of lipoproteins require proper supply of cholesterol esters produced through the ACAT catalyzed reaction.

ACAT is a membrane-bound enzyme located in the endoplasmic reticulum of various tissues of animal and human cells. The enzyme has been localized to the rough endoplasmic reticulum in rat liver. It is highly regulated in many cell types and tissues, and it is believed to play an important role in cholesterol metabolism in various cells and tissues such as the small intestinal mucosa, hepatocytes, macrophages, and the steroid hormone-producing tissues (O'Brien, P. M. and Sliskovic, D. R. (1992) in Current Opinion in Therapeutic Patents; Cadigan, K. M., et al. (1988) *J. Biol. Chem.* 263:274–282; Cadigan, K. M., et al. (1989) *J. Cell Biol*, 108:2201–2210).

Although ACAT has been studied intensively, much remains to be learned about its molecular structure. The active site of the enzyme has been localized to the cytoplasmic surface of the microsomal vesicles in the rat liver, using a combination of detergent and protease treatments, but whether the enzyme spans the entire membrane has not yet been determined. Lichtenstein, A. H. and Brecher, P. (1980) *J. Biol. Chem.* 255:9098–9104. Recent chemical modification studies indicate that essential histidyl and sulfhydryl residues may reside at or near the active site of the enzyme. Studies of ACAT activities of rabbit tissues suggest the existence of different ACAT subtypes since various tissues have differing sensitivities to histidyl-modifying reagents. Kinnunen, P. M. et al. (1988) *Biochemistry* 27:7344–7350.

ACAT activity has been studied from ACAT solubilized and reconstituted from various cultured cells, including rat and pig liver cells. Although these procedures have allowed enzyme activity to be measured in a defined lipid environment, little progress has been made as yet in purifying the solubilized preparations. To date, no laboratory had succeeded in purifying ACAT to homogeneity with retention of biological activity.

SUMMARY OF THE INVENTION

This invention pertains to purified, biologically active acyl coenzyme A:cholesterol acyltransferase (ACAT) and to nucleic acid (DNA or RNA) encoding acyl coenzyme A:cholesterol acyltransferase. The nucleic acid, or a fragment thereof, may be ligated with an expression vector and transfected into cells to express acyl coenzyme A:cholesterol acyltransferase activity in intact cells and in cell-free extracts. The nucleic acid, or fragments thereof, are useful as probes, as primers for polymerase chain reactions, or as antisense constructs.

Cells containing the nucleic acid, or active fragment thereof, as well as various cell-free systems are useful for screening and testing chemical agents serving as specific ACAT inhibitors. Such ACAT inhibitors are desirable in the development of drugs serving as specific ACAT inhibitors for prevention and/or treatment of various cholesterol-related disorders.

In addition, the nucleotide sequence of the gene encoding ACAT enables the screening of human populations for abnormal human ACAT activities for disease diagnosis. This invention provides a basis for creating various transgenic animals including mice and rabbits that permanently express the human ACAT gene. Such animals can be used to screen and test various agents that inhibit human ACAT activity in a tissue specific or non-tissue-specific manner in intact animals. In addition, this invention provides a basis for creating transgenic animals including chickens, cows and pigs with permanently reduced ACAT activity. Animals with lower ACAT activity have much less body cholesterol ester content, and thus would offer the same nutritional value but with less dietary cholesterol intake to consumers.

BRIEF DESCRIPTION OF THE DRAWINGS

FIG. 3. Nucleotide sequence of cDNA C$_1$, as determined by double stranded DNA sequencing.

FIG. 6. The nucleotide sequence of cDNA $K_1$. The region which overlaps with that of cDNA $C_1$ is underlined.

FIG. 9. The nucleotide and predicted amino acid sequences of cDNA $K_1$. Nucleotide residues are numbered on the right; amino acid residues are numbered on the left with residue 1 being the putative initiator methionine. The 5 stretches of sequences sharing significant homology with firefly luciferase "signature sequences" regions 1, 2 or 3 (Babbitt et al., (1992) *Biochemistry* 31:5594–5604) are underlined in the protein coding region. Leucines involved in the potential leucine heptad motif are identified by asterisks. The potential N-linked glycosylation site is indicated by a double asterisk (amino acid residue 409). The two AATAAA sites are underlined in the 3'-untranslated region.

DETAILED DESCRIPTION

Figure 1:
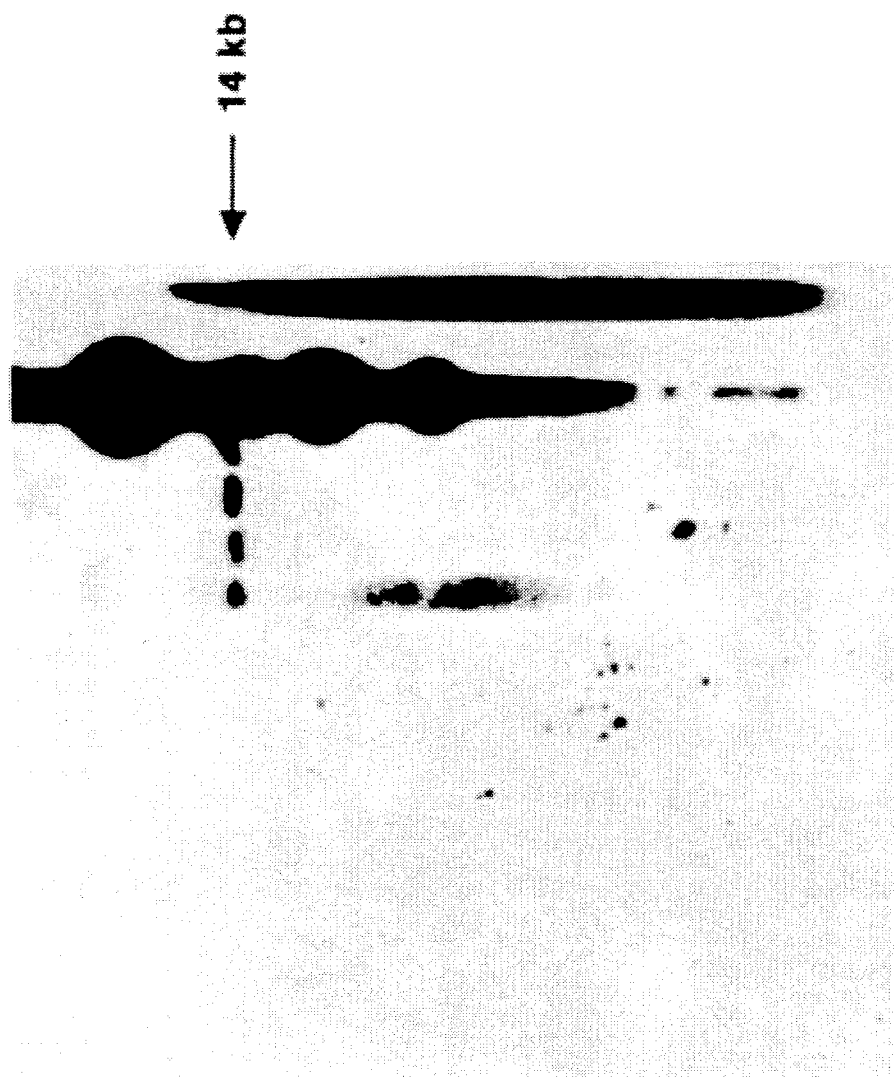
FIG. 1. Southern analysis of enzyme restricted genomic DNAs probed with $^{32}$P-gDNA G. Genomic DNAs were from 25-RA (lane 1 ), AC29 (lane 2), 29T2-8 Amph$^R$ 4,6,8,10,11,12,16 (lanes 3–9), 29T1 (lane 10), 29T2-4 (lane 11), 29T2-8 (lane 12), 29T2-10 (lane 13), human fibroblast (lane 15). Genomic DNAs were digested with EcoRI and Hind III, run on a 0.8% agarose gel, transferred to a nylon filter and probed with radiolabeled gDNA G. Fifteen µg of genomic DNA was used for each sample except for human fibroblasts(5 µg). Lane 14 contains 10 µg of λDNA (Hind III cut) as a size marker.

The enzyme acyl coenzyme A:cholesterol acyltransferase (ACAT) is an intracellular enzyme which previously had not been purified to homogeneity with retention of biological activity. This invention pertains to isolated, biologically active acyl coenzyme A:cholesterol transferase, or a biologically active portion thereof. As used herein, biological activity includes catalytic activity. ACAT has been shown to have amino acid sequences TNLIEKSASLDNGGCALTT, GRLVLEFSLLSYAF, GFGPTY, GYVAMKFAQVFGCF, and ARVLVLCUFNSILPGVL, and their functional equivalents, which are believed to be involved in catalytic activity. The enzyme, or active portion, is preferably human in origin.

The invention also pertains to the nucleic acid (DNA or RNA) encoding acyl coenzyme A:cholesterol acyltransferase and to the use of the nucleic acid to produce, by recombinant techniques, acyl coenzyme A:cholesterol acyltransferase.

One embodiment of the invention is the cDNA for human ACAT contained within the clone $K_1$, or any functional derivative of this cDNA. This nucleotide sequence is shown in Sequence Listing No. 2. Variants of this ACAT nucleotide sequence are also within the scope of this invention. Including sequences substantially homologous to the sequence of Sequence Listing No. 2. This includes sequences, such as those derived by mutagenesis, which have nucleotide insertions, deletions, substitutions, or other modifications, but which encode a catalytically active ACAT. The variants include fragments of the ACAT nucleotide sequence. As used herein, a fragment of the nucleotide sequence encoding human acyl coenzyme A:cholesterol acyltransferase refers to a nucleotide sequence having fewer nucleotides than the nucleotide sequence of the entire enzyme. Nucleic acid sequences used in any embodiment of this invention can be cDNA as described herein, or alternatively, can be any oligonucleotide sequence having all or a portion of a sequence represented herein, or their functional equivalents. Such oligonucleotide sequences can be produced chemically or mechanically using known techniques. A functional equivalent of an oligonucleotide sequence is one which is capable of hybridizing to a complementary oligonucleotide to which the sequences shown in the Sequence Listing, or fragment thereof, hybridizes, or a sequence complementary to either of the sequences shown in Sequence ID Nos. 2 or 3 the Sequence Listing. ACAT, or a portion of ACAT, can be produced by standard recombinant techniques using the nucleotide sequences of this invention. The nucleotide sequence encoding ACAT is inserted into an expression vector. A suitable host cell, such as a mammalian cell, is transformed with the vector, and the cell is cultured under conditions conducive to the production of the enzyme by the cell. ACAT, or a portion of ACAT, can be produced in other organisms, including bacteria, yeast, and insect cells, as well as various cell-free systems. A portion of ACAT expressed in these systems may express partial ACAT function, such as the ability to bind, inter alia, cholesterol, fatty acids, and coenzyme A, thus creating unique tools and assays for testing and screening for inhibitors which block these partial ACAT functions. These inhibitors would be genuine ACAT inhibitors.

The nucleotide sequence information contained in the cDNA encoding ACAT also provides crucial information concerning the catalytic mechanism of ACAT and provides investigators with a means for rational design of drugs serving as specific ACAT inhibitors. Such ACAT inhibitors are desirable for prevention and/or treatment of human hypercholesterolemia and human atherosclerosis. The nucleotide sequence information contained in the nucleic acid encoding ACAT enables design of various specific oligonucleotides as specific anti-sense DNAs or anti-sense RNAs, to inhibit human ACAT messenger RNAs, thereby to inhibit ACAT protein production, as described in more detail below.

The nucleic acid molecules of this invention can be used to produce primers for polymerase-mediated replication of nucleotide sequences encoding ACAT. Typically, the primer is a single stranded oligonucleotide substantially complementary to a portion of the ACAT sequence to be replicated. The primer will have a length sufficient to prime polymerase activity, generally a minimum of five to seven nucleotides, and typically from 16 to 30 nucleotides. Primers can be used in polymerase chain reaction (PCR) to amplify ACAT nucleotide sequences.

The nucleic acid molecules of this invention, and fragments thereof, are also useful as hybridization probes for library screenings to isolate and identify partial and/or full length cDNA or gDNA clones encoding ACAT genes from various animal species. Probes are generally labeled single stranded oligonucleotides substantially complementary to at least a portion of the ACAT nucleotide sequence. Hybridization reactions can be performed by standard techniques. Such probes can be used to identify different forms of human ACAT or ACAT from different animal species.

The probes and primers described above are useful as diagnostic tools to identify persons who have certain diseases, either acquired or genetically inherited, related to an abnormality in the ACAT gene or gene expression.

Nucleic acid molecules can be used to produce antisense constructs for inhibition of ACAT activity. In one embodiment, the oligonucleotide is an antisense oligonucleotide. The antisense oligonucleotide can be a normal oligonucleotide for an analogue of an oligonucleotide (e.g., phosphorothioate oligonucleotides, in which one of the phosphate oxygens is replaced by a sulfur atom) sufficiently stable to reach the target in effective concentrations. Antisense oligodeoxynucleotides can be prepared by standard synthetic procedures.

In another embodiment, the antisense construct is oligoribonucleotide. The antisense construct is produced by introducing the gene encoding the construct into a cell. For example, an ACAT nucleotide sequence can be placed in an expression vector in reverse orientation to generate an antisense transcript.

The antisense oligonucleotides can be designed to operate by different mechanisms of gene inhibition. Generally, these mechanisms involve the hybridization of the oligonucleotide to a specific RNA sequence, typically a messenger RNA. The targeted sequence can be located in the coding region of the RNA or it can be a signal sequence required for processing or translation of the RNA. Alternatively, the oligonucleotide may form a triple helix DNA structure, inhibiting transcription of the mRNA sequence.

The nucleic acid sequence of this invention can be used to produce transgenic animals either carrying human ACAT or having reduced levels of ACAT activity. Transgenic mammals, such as mice, expressing full or partial human ACAT activity can be easily created by methods well-documented in the art, for example those described in Leder et al., U.S. Pat. No. 4,736,866. One of ordinary skill in the art can prepare transgenic mammals by injecting the ACAT gene, or a portion thereof, into the germline of the mammal. Alternatively, the gene or gene fragment can be injected into the male pronucleus of the fertilized egg when the egg is at the single cell stage, prior to implanting the egg in the host female. Moreover, using similar methods, a transgenic animal, such as a chicken, cow, or pig, can be produced by, for example, transfecting germ cells with a nucleic acid sequence encoding an antisense construct which blocks ACAT expression. Transgenic mammals carrying those constructs would have decreased ACAT activity, and, as a result, lower body cholesterol levels. Such transgenic animals would offer the same nutritional values while decreasing consumers' dietary cholesterol intake.

The invention further comprises a stable mutant cell which lacks endogenous ACAT activity, and is transformed with a nucleic acid encoding human ACAT, such that the cell expresses activity of human ACAT, preferably at high levels, in intact cells and in cell-free extracts. The cell produces an excess of cholesterol ester, causing the cell to form detectable (e.g. visibly) cytoplasmic lipid droplets. These droplets disappear with inhibition of ACAT. This mutant cell containing the human ACAT gene can be used in an assay for agents, including antisense DNA and/or RNA, that inhibit human ACAT activity. The cell is exposed to the agent under conditions which allow the agent to be taken up into the cell, and the cell is examined for substantial disappearance of the lipid droplets. Substantial disappearance indicates inhibition of human acyl coenzyme A:cholesterol transferase. This invention also embraces any agents which inhibit ACAT identified by the above-described screening assay, or any other assay using the ACAT nucleic acid sequence, or fragments thereof.

The invention is illustrated further by the following exemplification.

EXEMPLIFICATION

EXAMPLE I.

A. Preparing Human ACAT Genomic DNA Fragments

Chinese hamster ovary (CHO) cells are a fibroblast-like cell line in which cholesterol ester synthesis is highly regulated by exogenous sources of cholesterol, such as low density lipoprotein (LDL), and by endogenous cholesterol synthesis. The inventor and others previously developed an amphotericin B enrichment procedure, and reported the isolation of ClIO cell mutants almost entirely lacking ACAT activity. All isolated mutants were found to belong to the same complementation group and possess a defect in the ACAT enzyme itself or in a factor needed for production of the enzyme (Cadigan, K. M., et al. (1988) *J. Biol, Chem,* 263:274–282).

Cells that regained the ability to synthesize cholesterol esters were isolated from the mutants described above. After populations of ACAT deficient mutant (AC29) were subjected to chemical mutagenesis, or transfected with human fibroblast whole genomic DNA, two revertants and one primary transfectant ($T_1$) were isolated. Isolation was achieved by virtue of the revertant cells' or transfectant cells' higher fluorescent intensities when stained with Nile Red, a stain specific for neutral lipids, including cholesterol esters.

Both revertants and transfectants regained large amounts of intracellular cholesterol ester and ACAT activity. However, heat inactivation experiments reveal that the enzyme activity of the transfectant cells has heat stability properties identical to those of human fibroblasts, while the ACAT activities of the revertants are similar to that of other Chinese hamster ovary cell lines. This demonstrates that the molecular lesion in the ACAT deficient mutants resides in the structural gene for the enzyme, and indicates that the transfectant cells corrected this lesion by acquiring and stably expressing a human gene encoding the human ACAT polypeptide.

Secondary transfectants (T2-4, T2-8, and T2-10) were isolated by transfection of ACAT deficient mutant cells with primary transfectant genomic DNA. Genomic Southern analysis of the secondary transfectants, using a probe specific for human DNA, revealed several distinct restriction fragments common to all the transfectants. These fragments were hypothesized to comprise part or all of the human ACAT gene (Cadigan, K. M., et al. (1989) *J. Cell Biol.* 108:2201–2210). These human gene fragments were isolated (see Section B below) and were used as the starting material for molecular cloning of the human ACAT cDNA of this invention.

Standard recombinant DNA techniques were employed, according to the methods known in the art and as described in Sambrook, J., et al. (1989) *Molecular Cloning: A Laboratory Manual,* 2nd ed., Cold Spring Harbor Laboratory, Cold Spring Harbor, N.Y. The use of λZAP, λDASH, pBluescript for library or recombinant plasmid constructions were following instructions manuals provided by Stratagene, Inc. The use of FAST-TRACK kit for mRNA isolation, of $pcDNA_1$ and $pcDNA_{neo}$ for library or recombinant plasmid constructions were following instruction manuals provided by Invitrogen Inc. Other biochemical assays and methods used here were all previously documented in Cadigan, K. M., et al. (1988) *J. Biol. Chem,* 263:274–282; Cadigan, K. M., et al. (1989) *J. Cell Biol.* 108:2201–2210; Hasan, M. T., et al. (1991) *Somatic Cell and Mol. Genetics*

17:413–517; Cadigan, K. M. and Chang, T. Y. (1988) *J. Lipid Res.* 29:1683–1692.

B. Isolating human ACAT cDNA $C_1$ Clone

A phage lambda (λDASH, from Stratagene, Inc.) library consisting of genomic DNA fragments of transfectant cell T2-8 was prepared and screened using the human-specific Alu-repetitive DNA as the probe prepared according to the method of Cadigan, K. M., et al. (1989) *J. Cell Biol.* 108:2201–2210. An Alu-positive, λ clone (designated as λG) containing an insert was isolated. The insert, designated as gDNA G, was determined to be approximately 14 kb in length. Insert gDNA G was labeled with $^{32}P$ and used as the probe in genomic Southern analyses of restriction-digested genomic DNAs of human skin fibroblasts, primary transfectant cell clone $T_1$, and of secondary transfectant cell clones T2-4, T2-8, and T2-10. Results (FIG. 1) show gDNA G is a specific, common-sized human DNA fragment present in the genomes of all four transfectant clones which exhibit human ACAT activity (Cadigan, K. M., et al. (1989) *J. Cell Biol.* 108:2201–2210). Fragment gDNA G was not found in the genomes of 25-RA cells or AC29 cells, which suggests that gDNA G may be part of the human ACAT genomic DNA.

TABLE 1

| Cell Type | [3H] Oleate Incorporated Into Cholesteryl Oleate in Intact Cells (% of 25RA) |
|---|---|
| 25-RA | 100.0* |
| 29T2-8 | 94.5 |
| 29T2-8Amph$^R$4 | 1.7 |
| 29T2-8Amph$^R$6 | 0.5 |
| 29T2-8Amph$^R$8 | 1.1 |
| 29T2-8Amph$^R$10 | 0.8 |
| 29T2-8Amph$^R$11 | 0.6 |
| 29T2-8Amph$^R$12 | 0.0 |
| 29T2-8Amph$^R$16 | 0.9 |
| 29T2-8Amph$^R$17 | 1.1 |
| 29T2-8Amph$^R$18 | 1.2 |

*100% = 7529 dpm/min/mg

To demonstrate the accuracy of this theory, nine individual ACAT deficient cells were isolated using the secondary transfectant cell T2-8 as the parental cell. The T2-8 cell was found to be very sensitive to amphotericin B killing. Using the same procedure as previously described for isolating ACAT deficient mutants from 25-RA cells (Cadigan, K. M., et al. (1988) *J. Biol. Chem.* 263:274–282), nine independent cell clones (designated as T2-8 $^{Ampho\ R4}$, T2-8 $^{Ampho.\ R6}$; etc.) were obtained from approximately 10×10$^6$ T2-8 cells. These clones are found to be devoid of ACAT activity when analyzed by $^3$H-oleate pulse in intact cells, as shown in Table 1.

Figure 2:
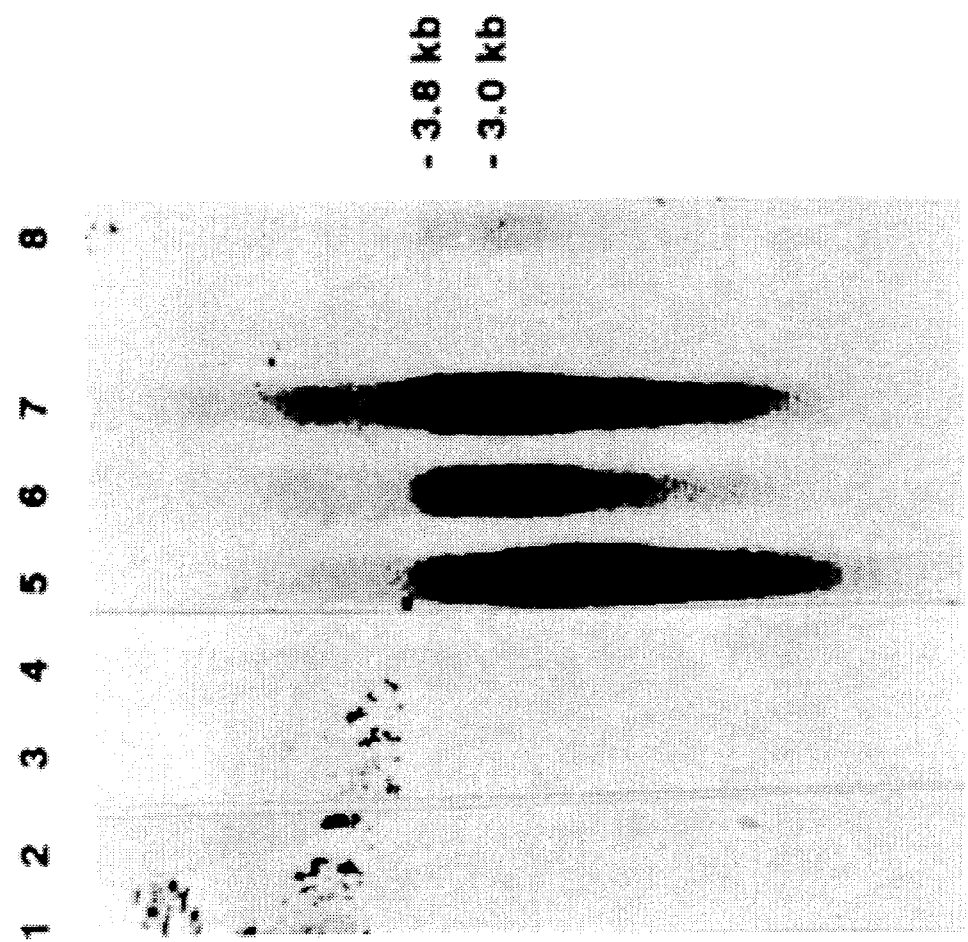
FIG. 2. Northern analysis of polyA$^+$ mRNAs probed with $^{32}$P-gDNA G$_2$. PolyA$^+$ mRNAs were prepared using FAST-TRACK (Invitrogen, Inc.) from confluent monolayer cells grown in media with 10% fetal calf serum of AC29 (lane 1), 25-RA (lane 2), T2-8 Amph$^R$4 (lane 3), T2-8 Amph$^R$10 ) (lane 4), T2-4, 8, 10 (lanes 5–7), and human A431 cells (lane 8). RNAs were run on a denaturing gel and blotted onto a nylon filter, cross-linked with UV light. Approx. 15 µg of RNA was used per lane. A control experiment showed that the same blot probed with $^{32}$P-actin cDNA provided a strong and sharp signal at the 1.9 kb region with approximately equal intensity for all 8 lanes.

Southern analyses (FIG. 1, lanes 3–9) using gDNA G as the probe showed that, in contrast to the parental T2-8 cells, none of these independent cell clones contains DNA fragment G as part of their genomes. This demonstrates 100% concordance between the presence/absence of DNA fragment G in the cell genome and the presence/absence of human ACAT activity in various CHO cells, and strongly supports the proposition that gDNA G is part of the human ACAT genomic DNA.

gDNA fragment G was digested with Hinfl. The resulting 1.2 kb fragment designated as gDNA $G_2$, which was found to be devoid of Alu-repetitive DNA, was isolated and cloned into the phagemid vector pBluescript (Stratagene). Fragment gDNA $G_2$ was found to contain at least one exonic element, since it strongly hybridized (particularly at the 3.8 kb and 3.0 kb regions) with polyA$^+$ mRNAs of discrete sizes prepared from all the human ACAT positive transfectant cells, and from human epidermal carcinoma A431 cells. The results of the Northern analysis of those polyA$^+$ mRNAs is shown in FIG. 2.

Figure 4:
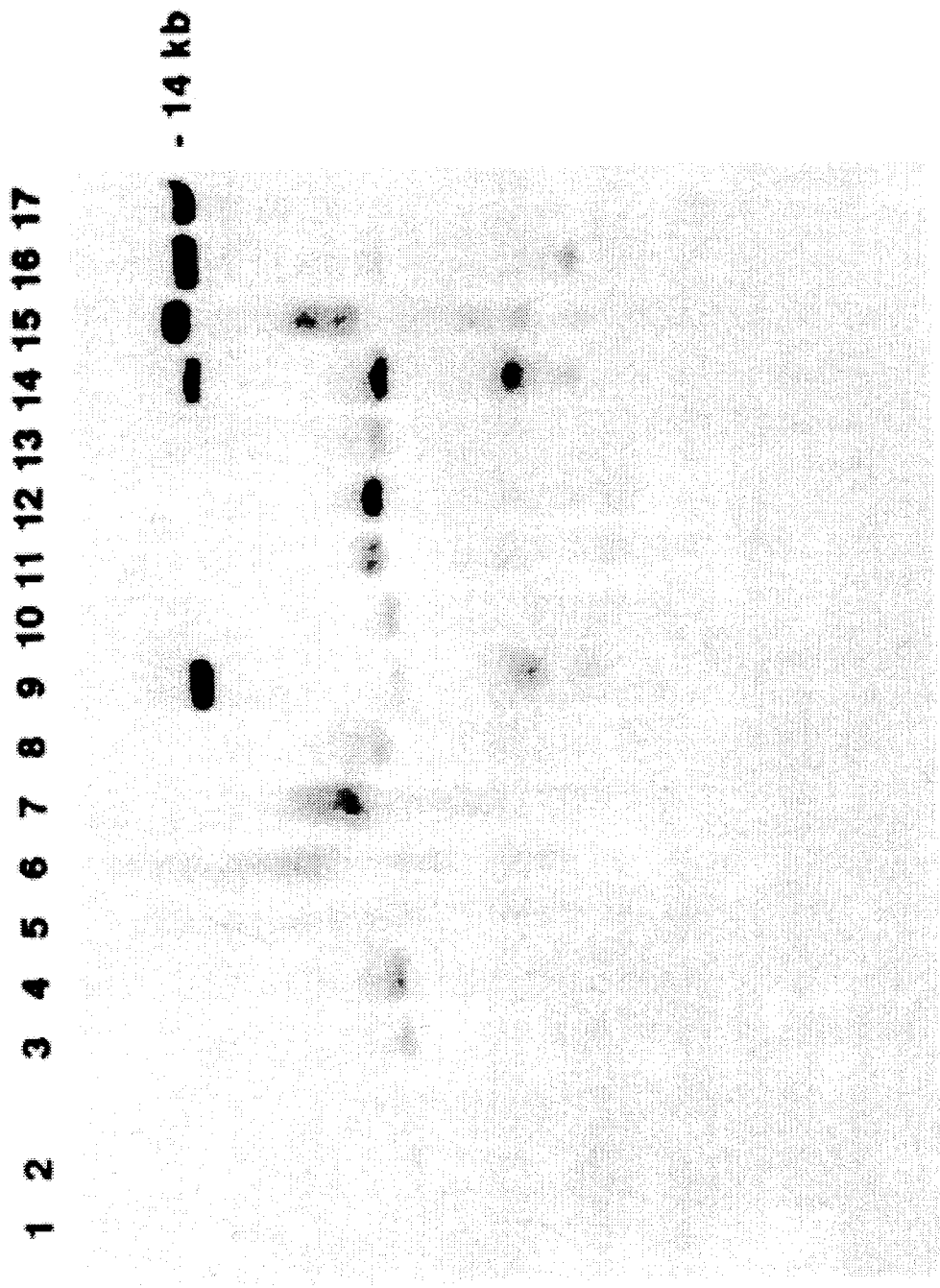
FIG. 4. Southern analysis of enzyme restricted genomic DNAs probed with $^{32}$P-cDNA C$_1$. Genomic DNAs were from 25-RA (lane 2), AC29 (lane 3), T2-8 Amph$^R$4, 6, 8, 10, 11, 12, 16, 17, 18 (lanes 4–8, 10–13), 29T1 (lane 9), 29T2-4, 8 10 (lanes 14, 15, 16), human fibroblast (lane 17). Lane 1 contains 10 µg of gDNA (Hind III cut) as a size marker. Genomic DNAs were digested and analyzed in the same manner as described in FIG. 2, except the $^{32}$P-probe was cDNA C$_1$.
Figure 5A:
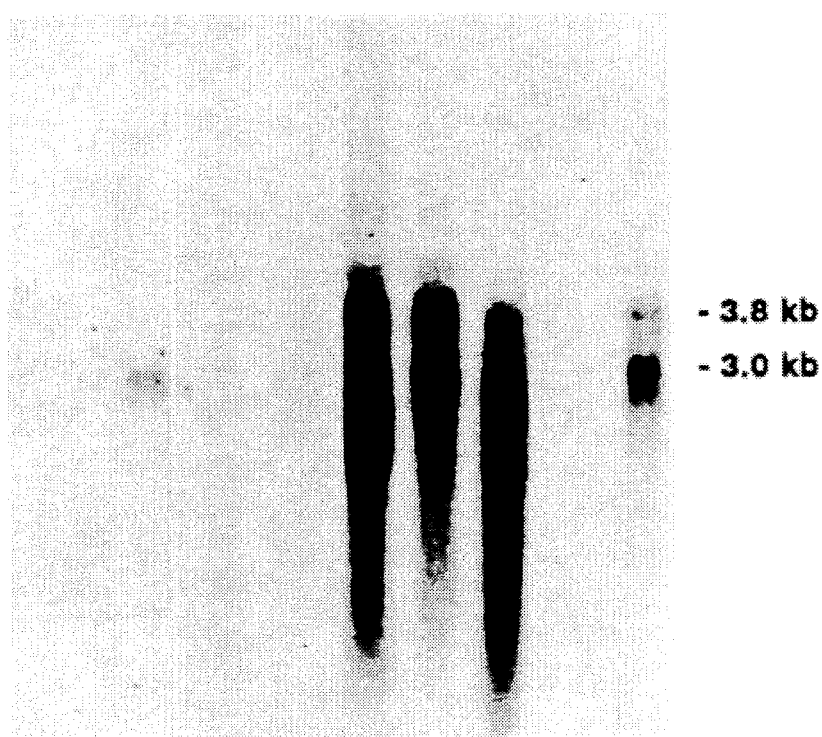
FIG. 5. Northern analysis of polyA+mRNAs probed with $^{32}$P-cDNA C$_1$. A duplicate blot prepared in an identical manner as described in FIG. 2 was probed with either $^{32}$P-cDNA $C_1$ (A), or $^{32}$P-actin cDNA (B).
Figure 5B:
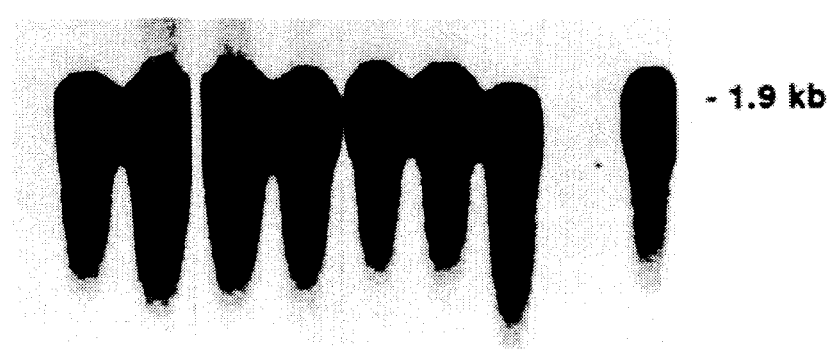

A cDNA library was prepared using polyA$^+$ mRNAs of T2-8 cells using pcDNA$_1$ (from Invitrogen, Inc.) as the vector. This library was screened with $^{32}$P gDNA $G_2$. A single cDNA clone (size=1006 bps) was identified, designated as cDNA $C_1$, and sequenced. As shown in FIG. 3 and the Sequence Listing, the nucleotide sequence contains a single, uninterrupted open-reading frame for a predicted polypeptide of 335 amino acids. Extensive search for nucleotide sequence homology between $C_1$ DNA and other DNAs of known sequences in several DNA sequence data banks reveals that the $C_1$ sequence has never been reported in the art. Genomic Southern analyses, FIG. 4, show that $^{32}$P-$C_1$ DNA strongly hybridizes with the same 14-kb genomic DNA fragment recognized by gDNA G in all the transfectant cell DNAs, and in human fibroblast DNAs. Northern analyses, shown in FIG. 5, demonstrate that $^{32}$P-$C_1$ DNA strongly hybridizes with the same polyA$^+$ mRNA species as recognized by the gDNA $G_2$ fragment in transfectant cell RNAs. These hybridization signals were absent in CHO cells devoid of human ACAT activity (FIG. 4, lanes 2–8 and 10–13; FIG. 5, lanes 1–4), consistent with the interpretation that $C_1$ DNA is part of the human ACAT cDNA. Clone $C_1$ DNA was ligated in two opposite orientations with the mammalian expression vector pcDNA$_{neo}$ (from Invitrogen), and then transfected into AC29 cells. These experiments repeatedly failed to produce functional complementation of ACAT deficiency in AC29 cells, thus indicating that $C_1$ DNA does not contain sufficient coding sequences to express human ACAT activity in CHO cells.

EXAMPLE II

Isolating Human ACAT cDNA $K_1$ Clone

A phage lambda library (in λZAP; Stratagene) containing cDNAs of human macrophage cell line THP-1 cells was obtained from Dr. T. Kodama of Tokyo University in Japan as a generous gift. (Preparation and use of this particular library is described in Matsumoto, et al. (1990) *Proc. Natl. Acad. Sci.* 87:9133–9137). This library was screened using both gDNA $G_2$ and cDNA $C_1$ as the probe. A single clone was identified which strongly hybridizes with both $G_2$ and $C_1$ probes. This clone, designated as cDNA $K_1$, is approximately 4.1 kb in length.

The entire $K_1$ nucleotide sequence has been completed, with 98% to 99% certainty, and is shown in FIG. 6 and in the Sequence Listing. Uncertain nucleotides are represented by the letter N. The $K_1$ nucleotide comprises a 1006-bp nucleotide sequence (underlined) which shares 100% homology with that of the DNA $C_1$ sequence shown in FIG. 3. $K_1$ cDNA can be stably propagated as an insert in the phagemid pBluescript.

To demonstrate that $K_1$ DNA complements ACAT deficiency in AC29 cells, the pBluescript plasmid containing $K_1$ DNA as the insert (designated as p$K_1$) was digested with enzymes NotI and EcoRV, to release the intact $K_1$ DNA insert free of NotI and EcoRV sites from the vector. The DNA mixture was ligated with a NotI-EcoRV linearized pcDNA$_1$ vector for the purpose of ligating $K_1$ DNA with the CMV promoter in proper orientation. The ligated DNA mixture was directly transfected into AC29 cells. Appropriate control transfections, using various DNA mixtures without $K_1$ DNA or without pcDNA$_1$ were performed in parallel. The result (Table 2) indicates that DNA $K_1$ is necessary to provide large increases in rate of cholesteryl ester synthesis in AC29 cells, in both transient and stable transfection experiments.

TABLE 2

Transfection of Various DNA Mixtures Into ACAT Deficient Mutant (Clone AC29)

| DNA Mixture | Relative Rate of Cholesterol Ester Synthesis In Intact Cells | | Relative Rate of Phospholipid Synthesis In Intact Cells |
|---|---|---|---|
| | A. Transient Transfection | B. Stable Transfection | |
| None | 1.0* | 1.0** | 1.0*** |
| pSV2 neo | 1.0 | 1.5 | 1.2 |
| pSV2 neo + pBluescript | 0.9 | 1.3 | 1.7 |
| pSV2 neo + pcDNA$_1$ | 1.1 | 1.6 | 0.9 |
| pSV2 neo + pBluescript + pcDNA$_1$ | 1.0 | 1.0 | 1.6 |
| pSV2 neo + pBluescript+ K$_1$ | 2.4 | 8.6 | 1.4 |
| pSV2 neo + pBluescript + pcDNA$_1$ + K$_1$ | 6.0 | 21.8**** | 1.0 |

*1.0 = 134 dpm/min/mg
**1.0 = 80 dpm/min/mg
***1.0 = 23 × 10$^2$ dpm/min/mg; measured only in stable transfectant cells
****12.4% of value found in 25-RA cells In the experiments reported in Table 2, DNA transfection of AC29 cells was accomplished according to the method of Hasan et al. ((1991) *Somatic Cell and Mol. Genetics* 17:413–517). AC29 cells plated at 0.3×10$^6$ cells/25 cm$^2$ flask in medium A were grown for 24 h before transfection. Each transfection was performed in triplicate, and included supercoiled plasmid pSV2$_{neo}$ (at 0.7 μg/flask) along with indicated DNA mixtures (which totaled 17.5 μg/flask). Each indicated plasmid was sequentially cut with EcoRV and NotI, salt precipitated, and redissolved in sterile water.

For the DNA mixture involving pBluescript+pcDNA$_1$, or pBluescript+pcDNA$_1$+K$_1$, ligation took place as follows: 50 μg pcDNA$_1$ was ligated with either 12.5 μg pBluescript, or with 25 μg pK$_1$ (cut with EcoRV and NotI to release K$_1$ insert from vector) in 20 μl volume using 3400 units of T4 DNA ligase (New England Biolab) at 16° C. overnight. The ligated DNA mixtures were salt precipitated, redissolved in sterile water and used directly in transfection experiments.

To measure cholesterol ester synthesis in transient transfectant cells, transfected cells were grown in medium A for 2 days, then in medium A+500 μg/ml G418 for one more day, and were subjected to $^3$H-oleate pulse assay in duplicate flasks. To measure cholesterol ester synthesis in stable transfectant cells, cells after transfection were grown in medium A for 2 days, then in medium A+500 μg/ml G418 for 14 days. The G418 resistant cells were then placed in medium A in duplicate flasks, and were subjected to $^3$H-oleate pulse assay.

In a separate experiment, DNA mixtures of pBluescript+ pcDNA$_{neo}$, or of pBluescript+pcDNA$_{neo}$+K$_1$ were treated, ligated, and used for stable transfection in an identical manner to that described in Table 2. Stable transfectant cells (resistant to 500 μg/ml G418 toxicity) were isolated and subjected to $^3$H-oleate pulse assay. Results very similar to those shown in Table 2 were obtained: While the transfectant clones resulting from the former DNA mixture only provided basal values, those cells resulting from the latter DNA mixture provided a large increase (by approximately 10-fold) in the rate of cholesterol ester synthesis as compared to the basal value found in AC29 cells.

In the stable transfectant cell populations containing pcDNA$_1$ and K$_1$ DNA, or containing pcDNA$_{neo}$ and K$_1$ DNA, a great deal of heterogeneity was observed in cytoplasmic cholesteryl ester contents, present as lipid droplets, in various cell clones. This can be visually detected by examination of cells under phase-contrast microscopy. That this is so appears to be due to variability of expression of the transfected K$_1$ gene in different clones.

Example III

Stable Transfectant 14e

The stably transfected cells described above were cloned by cloning rings. Eight independently cloned transfectant cells were evaluated for their rates of cholesterol ester synthesis in intact cells and in vitro by reconstituted ACAT assay. The result (shown in Table 3) indicates that one clone, identified as 14e, expresses the highest ACAT activity in intact cells and in vitro. Its ACAT activity is higher than those found in the transfectant clone T2-8 obtained previously through total human genomic DNA transfection experiments. A second stable transfectant clone (4b), obtained using the ligated DNA mixture of pcDNA$_{neo}$+ pBluescript+K$_1$, expresses significant ACAT activity, but this activity is less than that measured in the T2-8 cells.

TABLE 3

Rates of Cholesterol Ester Synthesis of Individual AC29 Clones Stably Transfected with K1 cDNA

| Cell Type | In Intact Cells (by Oleate Pulse) | InVitro (By Reconstituted ACAT Assay) |
|---|---|---|
| AC29 | 1.0* | 1.0** |
| 29K1-10 | 0.7 | 1.0 |
| 29K1-11 | 1.1 | 1.0 |
| 29K1-12 | 0.8 | 1.1 |

TABLE 3-continued

Rates of Cholesterol Ester Synthesis of Individual AC29
Clones Stably Transfected with K1 cDNA

| Cell Type | In Intact Cells (by Oleate Pulse) | InVitro (By Reconstituted ACAT Assay) |
|---|---|---|
| 29K1-6 | 1.1 | 1.9 |
| 29K1-13 | 5.4 | 3.1 |
| 29K1-5 | 0.9 | 4.3 |
| 29K1-4b | 42.4 | 13.6 |
| 29K1-14e | 82.4 | 23.3 |
| 29T2-8 | 70.6 | 16.1 |
| 25-RA | 84.2 | 44.4 |

*1.0 = 133 dpm/min/mg
**1.0 = 4 pmole/min/mg

In the experiments reported in Table 3, Clones $29K_1$-10, 11, 12, 13, and 14e were isolated from stable transfectant cells described in Table 2 using $pSV2_{neo}$+pBluescript+$K_1$ as the DNA mixture; clones 29 $K_1$-4b, 29 $K_1$-5, 29 $K_1$-6 were isolated from stable transfectant cells using pBluescript+$pcDNA_{neo}$+$K_1$, performed in a separate experiment in similar manner as described in Table 2; clones 14a, 14d, and 14e were isolated from stable transfectant cells described in Table 2 using $pSV2_{neo}$+pBluescript+$pcDNA_1$+$K_1$ as the DNA mixture. The oleate pulse assay and in vitro reconstituted ACAT activity assay were performed in duplicate as described earlier (Cadigan, K. M., et al. (1988) *J. Biol. Chem.* 263:274–282; Cadigan, K. M., et al. (1989) *J. Cell Biol.* 108:2201–2210).

Figures 7A, 7B, 7C, 7D:
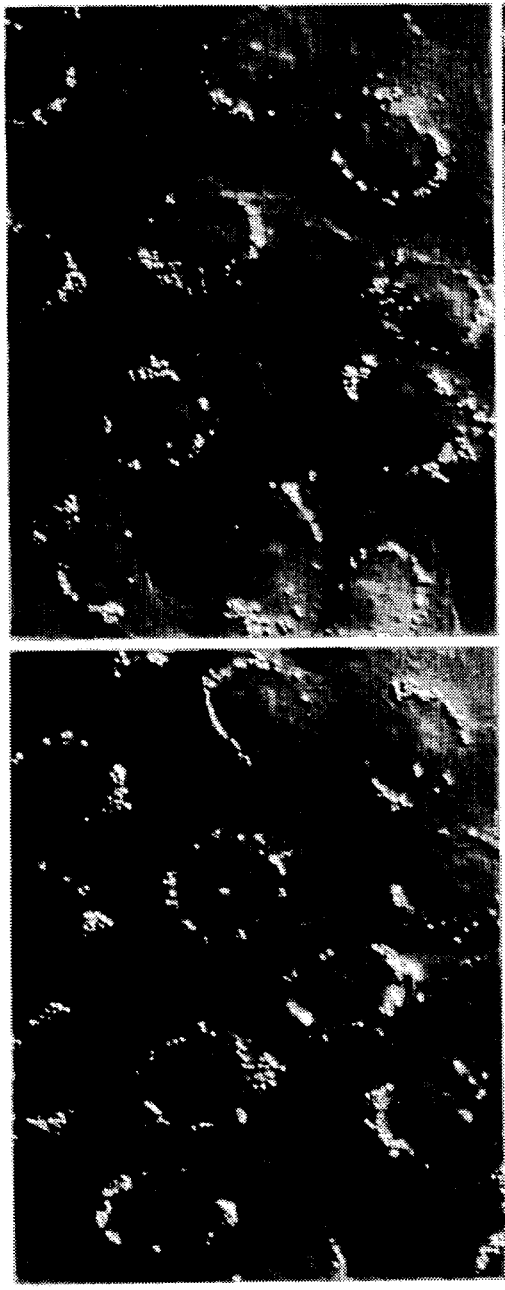
FIG. 7. 25-RA cells (A), AC29 cells (C) the stable transfectant cells 29 $K_1$-14e treated with (D) or without (B) ACAT inhibitor 58-035 viewed with differential-interference contrast microscopy. Cells were plated and processed for differential-interference contrast microscopic viewing by the same procedure as described in Cadigan, K. M., et al. (1989) *J. Cell Biol.* 108:2201–2210. In (D), cells were treated with 58-035 at 400 ng/ml for 36 h.
Figure 8:
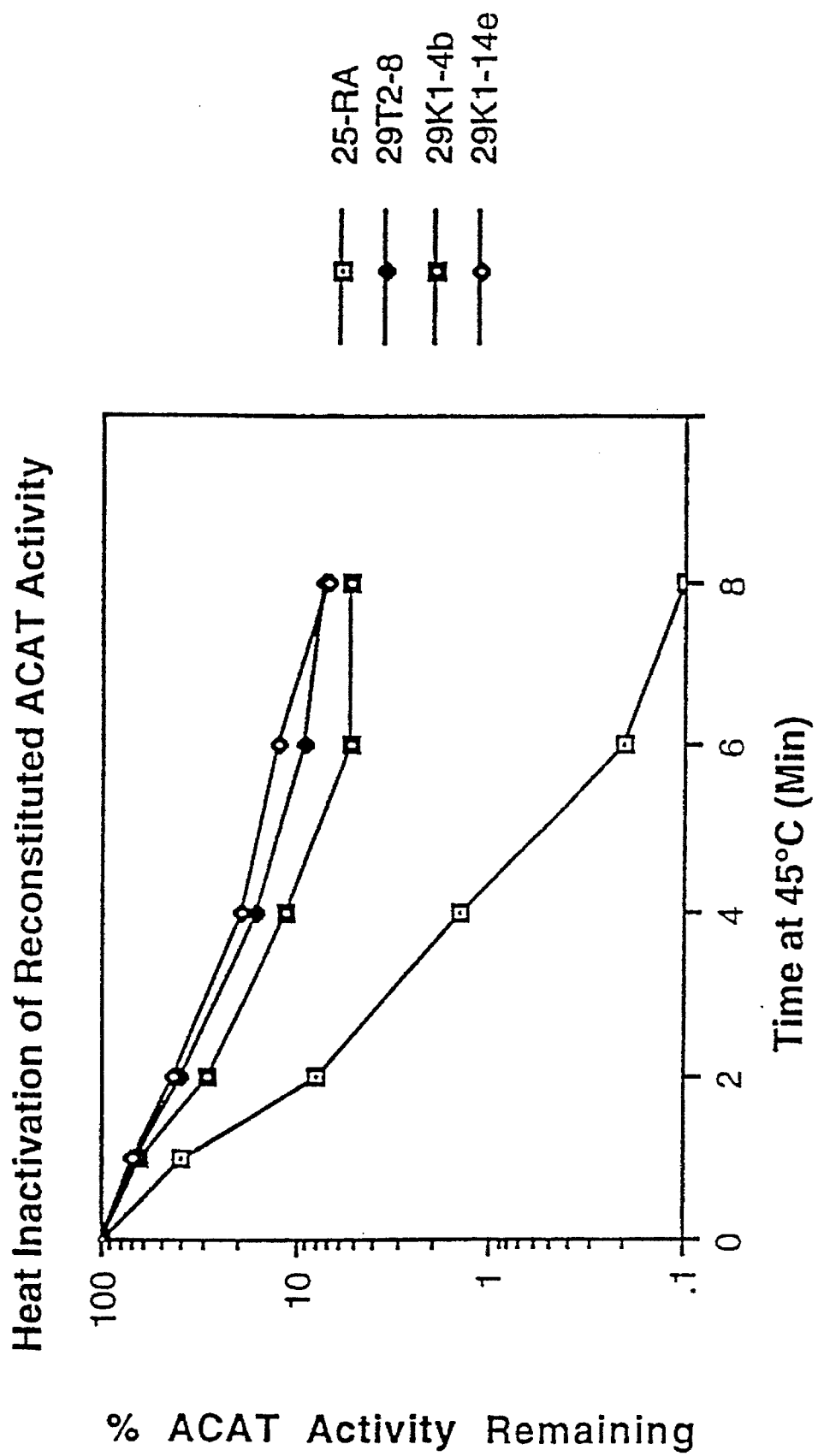
FIG. 8. Heat inactivation of reconstituted ACAT activity from 25-RA (symbol=open square), 29 T2-8 (symbol=closed diamond), 29 $K_1$-4b (symbol=closed square), and 29 K1-14e (symbol=partially open diamond). Cells were grown in 162 cm$^2$ flasks in medium A to confluence. They were harvested, and the cell extracts were reconstituted according to the procedure of Cadigan and Chang (1988) *J. Lipid Res.* 29:1683–1692. The reconstituted samples were incubated at 45° C. at indicated times, then placed on ice prior to assay for enzyme activity. The control activities for 25-RA, 29 T2-8, 29 $K_1$-4b, and 29 $K_1$-14e were 228, 73, 43. and 109 pmoles/min per mg respectively.

In 14e cells, numerous cytoplasmic lipid droplets are visible under the microscope (FIG. 7B). When treated with an ACAT inhibitor, specifically 58-035 at 400 ng/ml for 36 h, most of the lipid droplets in 14e cells disappear (FIG. 7D), indicating that these are cholesteryl ester droplets. For comparison purposes, photos of 25-RA cells, which contain ACAT of CHO origin, and AC29 cells, which are deficient in ACAT activity, as viewed under the microscope, are provided in FIGS. 7A and 7C. The cloned populations of 14e cells can be continuously grown in culture for at least two months without losing this distinct phenotype.

As was previously reported, the biochemical characteristics of ACAT activities present in the crude extracts of cultured human cells differs from that in CHO cells. Cadigan, K. M. et al. (1989) *J. Cell Biol.* 108:2201–2210: In reconstituted vesicles of defined lipid composition, the CHO cell ACAT activity exhibits a significantly greater thermolability at 45° C. than that of human cell ACAT activity. Based on this criterion, primary and secondary genomic ACAT transfectant cells (29T1, 29T2-4, 29T2-8, and 29T2-10) were determined to contain ACAT activities of human origin. Further investigation, by heat inactivation of the ACAT activities expressed in stable cDNA $K_1$ transfectant clones 14e and 4b, and comparison with that expressed in 25-RA cells and in T2-8 cells shows that the ACAT inactivation rates in 14e cells and 4b cells are the same as that of T2-8 cells, which is considerably slower than that found in 25-RA cells. This indicates that the ACAT activities expressed in $14_e$ cells and $4_b$ cells are of human origin. This result invalidates the alternative interpretation: that the $K_1$ cDNA was human cDNA which, upon transfection in AC29 cells, reactivated the CHO ACAT activity. If this were the case, the ACAT activity expressed in cells 14e and 4b would have behaved like that expressed in 25-RA cells, i.e., the CHO ACAT, in the heat inactivation study.

This cell clone can effectively be used as a tool to screen drugs and antisense constructs serving as human ACAT inhibitors. The numerous cytoplasmic lipid droplets in 14e cells that are visible under the microscope provide an elegant test for evaluating potential ACAT inhibitors. Specifically, when 14e cells are treated with an ACAT inhibitor, the lipid droplets essentially disappear, as illustrated in FIG. 7D. A simple, visual method for testing and screening potential human ACAT inhibitors in cultured cells is thus provided. Those skilled in the art will recognize that this embodiment is not limited to 14e cells, and can be used with any stable transfectant cell line that hyper expresses the ACAT gene, or a fragment thereof, for example, the 29K-4b or $29T_2$ cell lines. Those skilled in the art will also recognize that the visual detection of intracellular cholesteryl esters present in 14e cells, or other cell line capable of hyper expressing ACAT, could be achieved by means other than standard microscopy, such as phase-contrast microscopy, fluorescent dye staining followed by fluorescent microscopy, among others. The speed of detection may also be enhanced by coupling a rapid scanning mechanism to the microscopic apparatus.

EXAMPLE IV 1.7 kb $K_1$ cDNA Encoding Human ACAT

A fragment of the 4.0 kb $K_1$ cDNA was discovered that spans the entire predicted protein coding region of ACAT. It is the 1.7 kb Sal I-Hind III fragment, spanning nucleotide residues 1302–3050 of $K_1$.

Subcloning the 1.7 kb fragment into the $pcDNA1_{neo}$ vector, in both directions, produced plasmids designated $pcDNA1_{neo}$-$K_{1.7\ kb\ sense}$ and $pcDNA1_{neo}$-$K_{1.7\ kb\ antisense}$. To demonstrate ACAT expression, the plasmids, together with $pcDNA_{neo}$ as a control, were transiently transfected into AC29 cells. As shown in Table 4, transfection of $pcDNA1_{neo}$-$K_{1.7\ kb\ sense}$ dramatically increased the rate of cholesterol ester synthesis in AC29 cells, with values equal to 60% of those found in 25-RA cells. The plasmid minimally increased the rate of phospholipid synthesis. Control plasmids exhibited no similar effects. Plasmid $pcDNA1_{neo}$-$K_{1.7\ kb\ sense}$ also increased the rate of cholesterol ester synthesis in stable transfectant cells, approximately 20% of values found in 25-RA cells, without altering the rates of phospholipid synthesis.

TABLE 4

Transient Transfection of Plasmids Containing $pcDNA1_{neo}$ Vector and K1 $_{1.7kb}$ cDNA as Insert into ACAT Deficient Mutant (Clone AC29)

| | Relative Rate of Cholesterol Ester Synthesis In Intact Cells | | Relative Rate of Phospholipid Synthesis In Intact Cells | |
|---|---|---|---|---|
| DNA Mixture | A. Third day after Transfection | B. Fill Day after Transfection | A. Third day after Transfection | B. Fifth day after Transfection |
| $pcDNA1_{neo}$ | $1.0^a$ | $1.0^b$ | $1.0^c$ | $1.0^d$ |

TABLE 4-continued

Transient Transfection of Plasmids Containing pcDNA1$_{neo}$ Vector and K1 $_{1.7kb}$ cDNA as Insert into ACAT Deficient Mutant (Clone AC29)

| DNA Mixture | Relative Rate of Cholesterol Ester Synthesis In Intact Cells | | Relative Rate of Phospholipid Synthesis In Intact Cells | |
|---|---|---|---|---|
| | A. Third day after Transfection | B. Fill Day after Transfection | A. Third day after Transfection | B. Fifth day after Transfection |
| pcDNA1$_{neo}$-K1 $_{1.7kb}$ (antisense) | 0.9 | .07 | 1.0 | 1.0 |
| pcDNA1$_{neo}$-K1 $_{1.7kb}$ (sense) | 103 | 91* | 1.7 | 1.4 |

$^a$1.0 = 29 dpm/min/mg
$^b$1.0 = 45 dmp/min/mg
$^c$1.0 = 1404 dpm/min/mg
$^d$1.0 = 164 dpm/min/mg
*60.5% of value found in 25-RA The method of Hason et al. ((1991) *Somatic Cell and Mol. Genetics* 17:413–417) was used to perform transfection. 0.3×10$^6$ cells per 25 cm$^2$ flask were seeded in medium A for 24 h. 3 ml of fresh medium A with 100 µM Chloroquine was then added for 2 h before the transfection. For each flask, 3 µg of pcDNA1$_{neo}$ DNA or 5 µg of pcDNA1$_{neo}$-K$_{1.7\ kb}$ DNA was used in transfection. Incubation was at 37° C. for 16 h. Transfection cells were grown in medium A+500 µg.ml G418 for 3 or 5 days and were then subjected to $^3$H-oleate pulse assay in duplicate flasks. The construction of pcDNA1$_{neo}$-K$_{1.7\ kb}$ plasmids was described in Experimental Procedures.

As shown in FIG. 4., the K$_1$ cDNA contains a single open reading frame (ORF) (residues 1397–3046) 1650 bps in length and a predicted 64,805 dalton protein. This ORF is designated as ACAT K$_1$ protein. The second and third nucleotides before the putative first ATG codon and the one after it conformed to the Kozak sequences (Kozak, 1984). An in-frame stop codon was found 150 nucleotides upstream from the first ATG codon.

Hydrophobicity analysis of the hypothetical ACAT K$_1$ protein indicates that it contains at least two potential transmembrane α-helices located at amino acids 132–155 and 460–483 (FIG. 7). This analysis supports the conclusion that ACAT K$_1$ is an integral membrane protein. The polypeptide regions at amino acids 215–235, 320–340, and 355–380 are also very hydrophobic, yet these regions seem to be rich in β-sheet structure (panel B of FIG. 7), therefore, these regions may not contain transmembrane helices. One potential N-glycosylation site (Gavel and von Heijne, (1990) *Protein Engineering* 3:433–442) was identified (indicated by the symbol ** in FIG. 4). In contrast, the classic phosphorylation sites recognized by different protein kinases including c-AMP-dependent protein kinase and protein kinase C (reviewed in Kemp and Pearson, (1990) *Trends in Biochem. Sci.* 15: 342–346), could not be clearly identified. In addition, the proposed motif (Jackson and Peterson, (1990) *The EMBO J.* 9: 3153–3162) for retention of certain transmembrane proteins in the endoplasmic reticulum as well as the motif (Petrou et al., (1993) *Trends in Biochem. Sci.* 18: 41–42) for the fatty acid binding domain of certain intracellular lipid binding proteins could not be identified.

Tissue Distribution of ACAT K$_1$ Gene Transcripts

The human tissue distribution of K$_1$ gene transcripts was examined using $^{32}$P-cDNA C1 as the probe. The results (not shown) indicate that it cross-hybridized with poly(A)$^+$ RNAs of various discrete sizes, with strong signals at approx. 3 and 4 kb and with weak signals at approx. 4.7 and 7.4 kb. While the intensities varied, these signals were found in poly (A)$^+$ RNAs of virtually all of the tissues reported here.

EXAMPLE V

Homology With Other Enzymes

Figure 9A:
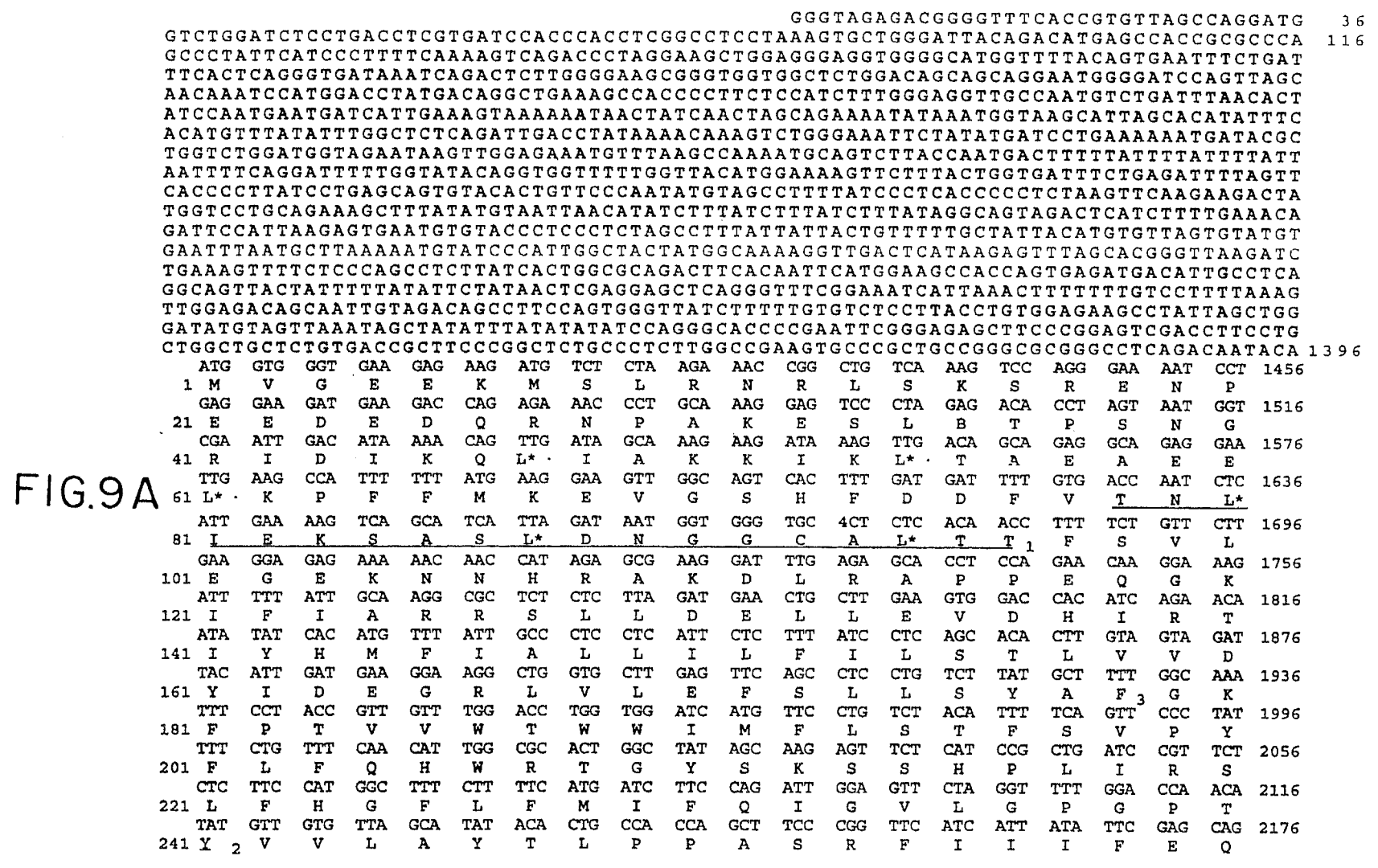
Figure 9B:
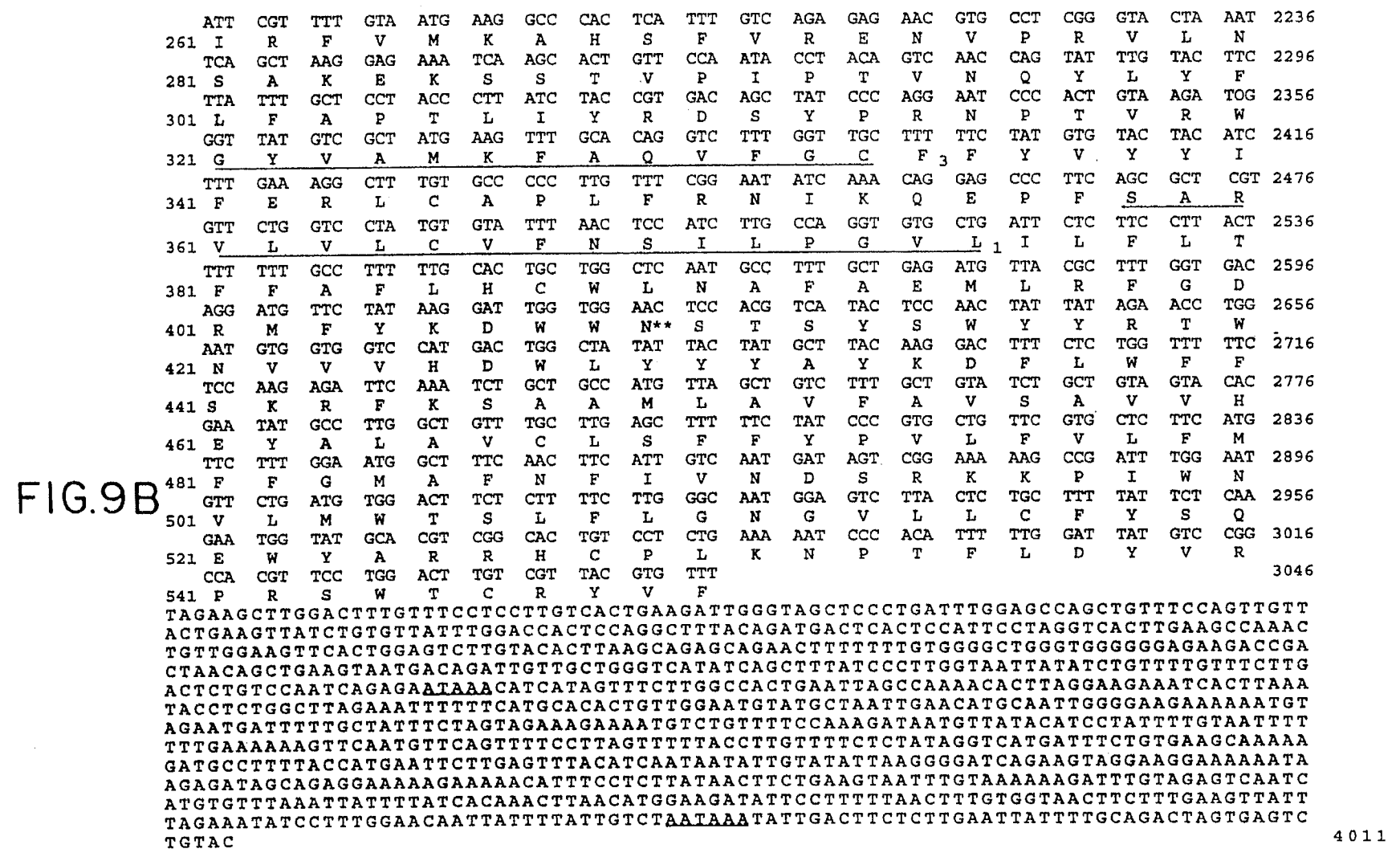

Protein homology analysis shows that the entire predicted ACAT K$_1$ protein sequence shares a 48% homology with human fatty acid ligase (Abe et al., (1992) *J. Biochem.* 111:123–129). In addition, further analysis shows that the predicted K$_1$ protein contains five separate stretches of linear sequences (TNLIEKSASLDNGGCALTT, GRLVLEFSLL-SYAF, GFGPTY, GYVAMKFAQVFGCF, and ARVLVL-CVFNSILPGVL, underlined in the protein coding region of FIG. 9) which share significant homology (42%, 57%, 80%, 57%, and 58% respectively, based on firefly luciferase sequences) with the newly identified "signature sequences" (Babbitt et al., (1992) *Biochemistry* 31: 5594–5604). These signature sequences include three separate segments of peptides and are present in at least twelve different enzymes including firefly luciferase and fatty acid ligase. These enzymes participate in various metabolic functions, and show one common feature—all are involved in the catalysis of acyl adenylate formation followed by acyl thioester formation and subsequent acyl transfer. This analysis suggests that these enzymes share common catalytic mechanisms, and these "signature sequences" constitute part(s) of the active site(s) of these enzymes. Within the ACAT K$_1$ protein sequence, two different stretches of peptides share homology with the "signature sequence" region #1 (amino acids 193–212 of luciferase), one stretch of peptides shares homology with signature sequence region #2 (amino acids 338–344 of luciferase), while two other stretches of peptides shared homology with the "signature sequence" region #3 (amino acids 338–401 of luciferase).

This finding is important for at least two reasons. First, it suggests that, in addition to functioning as a fatty acyl coenzyme A:cholesterol acyltransferase, the ACAT enzyme may also possess enzymatic activity mechanistically very similar to that of fatty acid: coenzyme A ligase, as well as those of the other enzymes listed in Table 1 of the Babbitt et al. article, supra. Second, this information provides an important clue for designing specific ACAT inhibitors based on known catalytic mechanisms utilized by these enzymes. For example, it should now be possible to design specific ACAT inhibitors based on structural characteristics of various inhibitors already known to inhibit the active site(s) of any of the enzymes listed in Table 1 of the Babbitt, et al. article, supra.

Equivalents

Those skilled in the art will recognize, or be able to ascertain using no more than routine experimentation, numerous equivalents to the specific procedures described herein. Such equivalents are considered to be within the scope of this invention and are covered by the following claims.

What is claimed is:

1. A non-human cell which either lacks or has deficient levels of endogenous acyl coenzyme A:cholesterol acyltransferase activity, said cell being transformed with an isolated nucleic acid molecule encoding endogenous human acyl coenzyme A:cholestrol acyltransferase such that the cell produces an excess of cholesterol esters causing the formation of detectable, cytoplasmic lipid droplets, wherein the cells is a 14e cell.

2. The cell of claim 1 wherein the cytoplasmic lipid droplets are visually detectable.

* * * * *

SEQUENCE LISTING ( 1 ) GENERAL INFORMATION:

( i i i ) NUMBER OF SEQUENCES: 22

( 2 ) INFORMATION FOR SEQ ID NO:1:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i i ) HYPOTHETICAL: NO ( i v ) ANTI-SENSE: NO ( x i ) SEQUENCE DESCRIPTION: SEQ ID NO:1:

TCACAGCCTT GGTGAGCCTT TATCTCAT                        28

( 2 ) INFORMATION FOR SEQ ID NO:2:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i i ) HYPOTHETICAL: NO ( i v ) ANTI-SENSE: NO ( x i ) SEQUENCE DESCRIPTION: SEQ ID NO:2:

CACTGCATGA GCAGTTACTC TCACACACT                       29

( 2 ) INFORMATION FOR SEQ ID NO:3:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i i ) HYPOTHETICAL: NO ( i v ) ANTI-SENSE: NO ( x i ) SEQUENCE DESCRIPTION: SEQ ID NO:3:

CGGCTAGCTC CCGAAGGTTA CTCCACCT                        28

( 2 ) INFORMATION FOR SEQ ID NO:4:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear (iii) HYPOTHETICAL: NO (iv) ANTI-SENSE: NO (xi) SEQUENCE DESCRIPTION: SEQ ID NO:4:

CCACAGTCTC GGTAATATGT TTAAGCCCCG GT 32

(2) INFORMATION FOR SEQ ID NO:5:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (iii) HYPOTHETICAL: NO (iv) ANTI-SENSE: NO (xi) SEQUENCE DESCRIPTION: SEQ ID NO:5:

CGCTCCAACA GTCCTCACGG TCTGCCTTCA T 31

(2) INFORMATION FOR SEQ ID NO:6:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (iii) HYPOTHETICAL: NO (iv) ANTI-SENSE: NO (xi) SEQUENCE DESCRIPTION: SEQ ID NO:6:

CAACGTCTGA ACAGTTACTC TCAAACGT 28

(2) INFORMATION FOR SEQ ID NO:7:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (iii) HYPOTHETICAL: NO (iv) ANTI-SENSE: NO (xi) SEQUENCE DESCRIPTION: SEQ ID NO:7:

CCGATGTTAA AATCCGTGCA AGCACTTCAT TT 32

(2) INFORMATION FOR SEQ ID NO:8:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (iii) HYPOTHETICAL: NO (iv) ANTI-SENSE: NO (xi) SEQUENCE DESCRIPTION: SEQ ID NO:8:

TGAGGGTTAT TGGTTTCGTT TACGGGCTA T 31

(2) INFORMATION FOR SEQ ID NO:9:

(i) SEQUENCE CHARACTERISTICS:
    (A) LENGTH: 33 base pairs
    (B) TYPE: nucleic acid
    (C) STRANDEDNESS: single
    (D) TOPOLOGY: linear (iii) HYPOTHETICAL: NO (iv) ANTI-SENSE: NO (xi) SEQUENCE DESCRIPTION: SEQ ID NO:9:

CAGGCTTCCC AACCTGTTCA ACTACCAACA ACT                33

(2) INFORMATION FOR SEQ ID NO:10:

(i) SEQUENCE CHARACTERISTICS:
    (A) LENGTH: 30 base pairs
    (B) TYPE: nucleic acid
    (C) STRANDEDNESS: single
    (D) TOPOLOGY: linear (iii) HYPOTHETICAL: NO (iv) ANTI-SENSE: NO (xi) SEQUENCE DESCRIPTION: SEQ ID NO:10:

CCACAATTTG GTGGTATCCT TAGCCCCGGT                    30

(2) INFORMATION FOR SEQ ID NO:11:

(i) SEQUENCE CHARACTERISTICS:
    (A) LENGTH: 32 base pairs
    (B) TYPE: nucleic acid
    (C) STRANDEDNESS: single
    (D) TOPOLOGY: linear (iii) HYPOTHETICAL: NO (iv) ANTI-SENSE: NO (xi) SEQUENCE DESCRIPTION: SEQ ID NO:11:

CAACCCGGCT GCCAGCATTT AACTGGTAAC CT                 32

(2) INFORMATION FOR SEQ ID NO:12:

(i) SEQUENCE CHARACTERISTICS:
    (A) LENGTH: 32 base pairs
    (B) TYPE: nucleic acid
    (C) STRANDEDNESS: single
    (D) TOPOLOGY: linear (iii) HYPOTHETICAL: NO (iv) ANTI-SENSE: NO (xi) SEQUENCE DESCRIPTION: SEQ ID NO:12:

TCGGTGGATC AGATTCTCAC TGATCTTTCG CT                 32

(2) INFORMATION FOR SEQ ID NO:13:

(i) SEQUENCE CHARACTERISTICS:
    (A) LENGTH: 30 base pairs
    (B) TYPE: nucleic acid
    (C) STRANDEDNESS: single
    (D) TOPOLOGY: linear (iii) HYPOTHETICAL: NO (iv) ANTI-SENSE: NO ( x i ) SEQUENCE DESCRIPTION: SEQ ID NO:13:

CCAACACTTA GCATTCATCG TTTACGGCAT 30

( 2 ) INFORMATION FOR SEQ ID NO:14:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i i ) HYPOTHETICAL: NO ( i v ) ANTI-SENSE: NO ( x i ) SEQUENCE DESCRIPTION: SEQ ID NO:14:

TTCGCTACGG CTCCGTTTTT TCAACTTAAC CT 32

( 2 ) INFORMATION FOR SEQ ID NO:15:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i i ) HYPOTHETICAL: NO ( i v ) ANTI-SENSE: NO ( x i ) SEQUENCE DESCRIPTION: SEQ ID NO:15:

CCCCTGCTTC TGGGCAGGTT ACCCACGT 28

( 2 ) INFORMATION FOR SEQ ID NO:16:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i i ) HYPOTHETICAL: NO ( i v ) ANTI-SENSE: NO ( x i ) SEQUENCE DESCRIPTION: SEQ ID NO:16:

TCGCTACCCA TGCTTTCGAG CCTCAGCT 28

( 2 ) INFORMATION FOR SEQ ID NO:17:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i i ) HYPOTHETICAL: NO ( i v ) ANTI-SENSE: NO ( x i ) SEQUENCE DESCRIPTION: SEQ ID NO:17:

CGCCGCGGGT CCATCCAGAA GTGATAGCCT 30

( 2 ) INFORMATION FOR SEQ ID NO:18:

( i ) SEQUENCE CHARACTERISTICS:
        ( A ) LENGTH: 32 base pairs
        ( B ) TYPE: nucleic acid
        ( C ) STRANDEDNESS: single (D) TOPOLOGY: linear (iii) HYPOTHETICAL: NO (iv) ANTI-SENSE: NO (xi) SEQUENCE DESCRIPTION: SEQ ID NO:18:

CTGAATTCAG TAACCCTAGA TGGGCCCCTA GT                32

(2) INFORMATION FOR SEQ ID NO:19:

(i) SEQUENCE CHARACTERISTICS:
                (A) LENGTH: 32 base pairs
                (B) TYPE: nucleic acid
                (C) STRANDEDNESS: single
                (D) TOPOLOGY: linear (iii) HYPOTHETICAL: NO (iv) ANTI-SENSE: NO (xi) SEQUENCE DESCRIPTION: SEQ ID NO:19:

TATCACTCAC CGTCTGACTC CCGGATATAA AT                32

(2) INFORMATION FOR SEQ ID NO:20:

(i) SEQUENCE CHARACTERISTICS:
                (A) LENGTH: 27 base pairs
                (B) TYPE: nucleic acid
                (C) STRANDEDNESS: single
                (D) TOPOLOGY: linear (iii) HYPOTHETICAL: NO (iv) ANTI-SENSE: NO (xi) SEQUENCE DESCRIPTION: SEQ ID NO:20:

TAGTTAGCCG TGGCTTTCTG GTTGGAT                      27

(2) INFORMATION FOR SEQ ID NO:21:

(i) SEQUENCE CHARACTERISTICS:
                (A) LENGTH: 28 base pairs
                (B) TYPE: nucleic acid
                (C) STRANDEDNESS: single
                (D) TOPOLOGY: linear (iii) HYPOTHETICAL: NO (iv) ANTI-SENSE: NO (xi) SEQUENCE DESCRIPTION: SEQ ID NO:21:

CGATTACCCT CTCAGGTCGG CTACGTAT                     28

(2) INFORMATION FOR SEQ ID NO:22:

(i) SEQUENCE CHARACTERISTICS:
                (A) LENGTH: 31 base pairs
                (B) TYPE: nucleic acid
                (C) STRANDEDNESS: single
                (D) TOPOLOGY: linear (iii) HYPOTHETICAL: NO (iv) ANTI-SENSE: NO (xi) SEQUENCE DESCRIPTION: SEQ ID NO:22:

TTCGGGCCTC CAGTGCGTTT TACCGCACCT T                 31